(12) United States Patent
Meyer et al.

(10) Patent No.: US 6,365,180 B1
(45) Date of Patent: Apr. 2, 2002

(54) ORAL LIQUID COMPOSITIONS

(76) Inventors: Glenn A. Meyer, 6117 Clairidge Rd., Wilmington, NC (US) 28403; Laura A. Trespidi, Finkenstrasse 7, 89073 Ulm (DE); Edward S. Wilson, 3208 Aster Ct., Wilmington, NC (US) 28409; Christy M. Clark, 135 Stuart Ave., Southport, NC (US) 28461; Ashok J. Desai, 3412 Hampshire Dr., Wilmington, NC (US) 28409; Frederick D. Sancilio, 2332 Ocean Point Dr., Wilmington, NC (US) 28405

( * ) Notice: Subject to any disclaimer, the term of this patent is extended or adjusted under 35 U.S.C. 154(b) by 0 days.

(21) Appl. No.: 09/354,982

(22) Filed: Jul. 16, 1999

Related U.S. Application Data

(63) Continuation-in-part of application No. 09/232,354, filed on Jan. 15, 1999.
(60) Provisional application No. 60/071,865, filed on Jan. 20, 1998.

(51) Int. Cl.$^7$ ............................ A61K 9/48; A61K 9/64; A61K 9/26; A61K 9/36
(52) U.S. Cl. ..................... 424/451; 424/452; 424/456; 424/463; 424/469; 424/480
(58) Field of Search ................. 424/451, 463, 424/489, 456, 480, 469, 452

(56) References Cited

U.S. PATENT DOCUMENTS

| | | | |
|---|---|---|---|
| 4,704,405 A | 11/1987 | O'Neill et al. ............... 514/568 |
| 4,880,835 A | 11/1989 | Park ........................... 514/570 |
| 5,071,643 A | 12/1991 | Yu et al. ..................... 514/570 |
| 5,183,829 A | * 2/1993 | Caldwell .................... 514/470 |
| 5,505,961 A | 4/1996 | Shelley et al. .............. 424/451 |
| 5,516,789 A | * 5/1996 | Brooks et al. .............. 514/414 |
| 5,609,882 A | 3/1997 | Aoki et al. ................. 424/451 |
| 6,013,280 A | 1/2000 | Frisbee et al. ............. 424/464 |
| 6,024,982 A | * 2/2000 | Oshlack et al. ............. 424/476 |

FOREIGN PATENT DOCUMENTS

| | | | |
|---|---|---|---|
| GB | 2059768 | 4/1961 | .......... A61K/31/60 |

OTHER PUBLICATIONS

International Search Report for PCT/US00/19372, mailed Feb. 5, 2001.

Najib et al.; Physicochemical characterization of ibuprofen–polyvinylpyrrolidone dispersions, International Journal of Pharmaceutics, 45, p. 139–144, 1988.

Chan, et al.; Application of Radiotelemetric Technique in Evaluating Diclofenac Sodium Absorption After Oral Administration of Various Dosage Forms in Healthy Volunteers, Pharmaceutical Research, 7:10, p. 1026–1032, 1990.

* cited by examiner

*Primary Examiner*—Thurman K. Page
*Assistant Examiner*—S. Tran
(74) *Attorney, Agent, or Firm*—Steven A. Fontana, Esq.; Myers Bigel Sibley & Sajovec

(57) ABSTRACT

The present invention relates to novel, liquid and semi-solid pharmaceutical compositions which can be administered in liquid form or can be used for preparing capsules containing such pharmaceutical compositions. Also provided are methods of using and processes for preparing the pharmaceutical compositions of the present invention.

53 Claims, No Drawings

ORAL LIQUID COMPOSITIONS

CROSS REFERENCE TO RELATED APPLICATIONS

The instant application is a continuation-in-part application of Ser. No. 09/232,354 filed Jan. 15, 1999, the disclosure of which is incorporated herein by reference in its entirety, which claims priority to U.S. Provisional Application Ser. No. 60/071,865 filed Jan. 20, 1998, the disclosure of which is incorporated herein by reference in its entirety.

FIELD OF THE INVENTION

The present invention relates to pharmaceutically elegant compositions for oral administration, and methods of using such compositions for enhancing the rate and degree of absorption of the pharmaceutically active component of such compositions, and for minimizing gastric irritation induced or caused by ingestion of such pharmaceutically active components. The pharmaceutically active component of compositions of the present invention include at least one pharmaceutically active agent having at least one acid moiety, preferably a carboxylic acid moiety, especially of the class of agents known as non-steroidal anti-inflammatory drugs (NSAIDs) which is soluble in acid at a ratio of about 30 to 1 (acid to solute) to about 10,000 to 1 (acid to solute).

BACKGROUND OF THE INVENTION

Within the pharmaceutical art, the formulation of pharmaceutically active compounds into usable dosage forms, in which the absorption of the active ingredient is optimized and the extent of controllable side effects is minimized, is challenging to pharmaceutical formulation scientists and, frequently, unpredictable. In particular, pharmaceutical formulations for pharmaceutical agents having at least one acid moiety, preferably a carboxylic acid moiety, and which is soluble in acid at a ratio of about 30 to 1 (acid to solute) to about 10,000 to 1 [acid to solute; sparingly soluble to practically insoluble or insoluble (see, e.g., Sokoloski, T. D., *Remington's Pharmaceutical Sciences*, 16:208; 1990)] are generally known in the art to have less-than-optimum absorption and, in some instances, to cause otherwise controllable side effects upon administration to mammals. Representatives of these compounds include, for example, pharmaceutical agents well known in the art as non-steroidal anti-inflammatory drugs (NSAIDs), acetylcholinesterace ("ACE") inhibitors represented by the "pril" family, HMG-COA reductase inhibitors represented by the "statin" family, histamine $H_1$-receptor antagonists such as, for example, fexofenadine, inhibitors of gastric acid secretion such as omeprazole, mast cell stabilizing agents, antihyperlipidemia agents, penicillins, antiacne agents, cephalosporins, including, for example, β-lactams, salicylates, and a multitude of individual pharmaceutical agents.

For example, U.S. Pat. No. 4,880,835 describes the preparation of oral liquid compositions of calcium sulindac using a pharmaceutical vehicle comprised of a glycol, a polyol, and an optional alcohol. The patent further describes the well recognized problem of absorption of pharmaceutical agents, as described above, particularly NSAIDs, from the gut.

K. Chan, et al., *Pharma Research*, 7:1027 (1990) demonstrated that sodium diclofenac (an NSAID) was more orally bioavailable from an enteric coated tablet than from an aqueous solution. This is contrary to the expectation of the art and confirms the fact that a problem in the art exists.

U.S. Pat. No. 4,704,405 also describes the problem of absorption of the above-described compounds, particularly NSAIDs such a sulindac, from the gastrointestinal tract.

N. M. Najib, et al., *International Journal of Pharmaceutics*, 45:139 (1988) have reported that ibuprofen-polyvinylpyrrolidone may form a weak acid-weak base type of complex in a solid state or in solution. This reference does not report any studies of the media or excipients used in the present invention.

U.K. Patent No. 2,059,768 describes the formation of more soluble derivatives of NSAIDs with the TRIS group of compounds.

Furthermore, U.S. Pat. No. 5,183,829 describes the preparation of NSAID formulations which appeared, in part, to improve adsorption of the pharmaceutically active agent while having positive effect on the aforementioned gastric side effects caused by NSAIDs. The patent describes a glycol-polyol media which can not be effectively used with soft gelatin capsules. More particularly, it was discovered that the polyols, and the concentration of polyols taught therein, caused the soft gelatin capsules to become tacky and adhere to adjacent soft capsules. This problem renders the pharmaceutical formulation taught in the '829 patent unviable when used in soft gelatin capsules.

Accordingly, the pharmaceutical formulations of the present invention represent a solution to the problems which result from formulations of the '829 patent as well as an advancement in the art of formulating pharmaceutically active substances into more elegant medicaments.

SUMMARY OF THE INVENTION

This invention relates to improved oral compositions which are useful as oral, liquid medicaments which can also be used to fill soft capsules or solidified, as taught here, to be used in hard capsules, particularly soft gelatin capsules and hard gelatin capsules, respectively, comprising one or more pharmaceutically active agents wherein said pharmaceutically active agent is selected from the group consisting of said agents wherein at least one of said agents having at least one acid moiety, and at least one of said agents having at least one ester group or other chemically active moiety in which the terminal moiety to said ester group or other chemically active moiety is hydrolyzed or otherwise removed in situ or in vivo forming at least one acid moiety; and wherein said pharmaceutically active agent is soluble in acid at a ratio of about 3:1 (acid to solute) to about 10,000:1 (acid to solute) or a pharmaceutically acceptable salt thereof (hereinafter, the "Active Ingredient");

at least one dispersing agent; and at least one solubilizing agent; and, optionally, at least one surfactant; and, further optionally, at least one plasticizing agent.

The present invention further relates to the use of the compositions of the present invention for improving adsorption of the Active Ingredients and for minimizing the controllable side effects induced by such Active Ingredients, particularly the NSAIDs, where appropriate. Also provided are methods of using the compositions of the present invention wherein said composition comprises as an Active Ingredient at least one NSAID and, optionally a motility and/or antinausea agent, for the treatment of paroxysmal headaches, particularly migraine headaches.

DETAILED DESCRIPTION OF THE INVENTION

One aspect of the present invention provides compositions which are useful as oral, liquid medicaments which can also be used to fill soft capsules or solidified, as taught herein, to be used in hard capsules, particularly soft gelatin capsules and hard gelatin capsules, respectively, comprising
one or more pharmaceutically active agents wherein said pharmaceutically active agent is selected from the group consisting of said agents wherein at least one of said agents having at least one acid moiety, and
at least one of said agents having at least one ester group or other chemically active moiety in which the terminal moiety to said ester group or other chemically active moiety is hydrolyzed or otherwise removed in situ or in vivo forming at least one acid moiety; and wherein said pharmaceutically active agent is soluble in acid at a ratio of about 3:1 (acid to solute) to about 10,000:1 (acid to solute) or a pharmaceutically acceptable salt thereof (hereinafter, the "Active Ingredient");
at least one dispersing agent; and
at least one solubilizing agent; and, optionally,
at least one surfactant; and, further optionally,
at least one plasticizing agent.

The Active Ingredients used in the present compositions are well known in the pharmaceutical art, are prepared via methods well known in the chemical and pharmaceutical arts, and include, for example, pharmaceutically active compounds as described above having at least one acid moiety wherein such acid moiety is, most preferably, a carboxylic acid. Other acid moieties are well known to one of ordinary skill in the art. Representative Active Ingredients include, for example, non-steroidal, anti-inflammatory drugs (NSAIDs) which are exemplified by the aralkylcarboxylic acids such as, for example, diclofenac, fenoprofen, flurbiprofen, ibuprofen, indomethacin, ketoprofen, ketorolac, naproxen, sulindac, etodolac, and tometin, and by the arylcarboxylic acids such as, for example, diflunisal, mefenamic acid, meclofenamic acid, and flufenamic acid. This list of NSAIDs is presented solely for the purpose of exemplification and is not intended to be limiting. Other NSAIDs, as well as other Active Ingredients which are used in the compositions of the present invention, are described, in addition to their dose regimens, in well known references such as, for example, the *Physician's Desk Reference* and the *Merck Index*. For example, the following families of compounds, individual compounds, are included, without limitation, as Active Ingredients for the compositions of the present invention:

"ACE" inhibitors including, for example, quinapril, ramipril, captopril, benazapril, trandolapril, fosinopril, lisinopril, moexipril, and enalapril;

HMG-COA reductase inhibitors including, for example, fluvastatin, lovastatin, pravastitin, cervistatin, atorvastatin, and simvastitin;

histimine H1-receptor antagonists, including, for example, fexofenadine;

mast cell stabilizing agents including, for example, cromolyn;

inhibitors of gastric acid secretion including, for example, omeprazole;

antihyperlipidemia agents including, for example, gemfibrozil;

hypolipemic agents including, for example, ciprofibrate;

fluoronated quinolones including, for example, ciprofloxacin, lomefloxacin, and ofloxacin;

peripheral decarboxylase inhibitors including, for example, carbidopa and levodopa;

antiacne agents including, for example, retinoic acid;

prostaglandin analogs including, for example, carboprost;

various well known penicillins (including, for example, amoxicillins and ampicillins), β-lactams, and cephalosporins; and various compounds such as, for example, liothryronine, probenecid, and the like.

Of course, the above list of Active Ingredients is presented for exemplification purposes, and is not intended to limit the scope of the present invention in any respect, and should not be so construed.

As shown above, compounds included in the present invention also include those pharmaceutically active substances which, when prepared as a pharmaceutical formulation, comprise at least one ester group or other chemically active moiety in which, when the terminal moiety to such ester group or other chemically active moiety is hydrolyzed or otherwise removed in situ or in vivo, forms at least one acid moiety, such as, for example lovastatin and simvastatin, (e.g. a lactone→—COOH). Such other chemically active moieties are well known in the art. As used herein, the term Active Ingredients includes the pharmaceutically acceptable salts of all of the compounds heretofore described. Preparation of the above-described Active Ingredients, including the preparation of appropriate pharmaceutically acceptable salts, is well documented in the chemical, medical, patent, and pharmaceutical literature.

In the compositions of the present invention, a pharmaceutically non-toxic amount of Active Ingredients is used. Accordingly, the concentration of each such Active Ingredient is known in the art or may be determined by employing standard practices which are well known in the art. More specifically, the concentration of Active Ingredient in the compositions of the present invention may range from about less than one percent to about greater than ninety-nine percent (wiw) but, typically range from about less than one percent to about forty percent, and preferably, from about less than one percent (1%) to about less than twenty percent (20%). Generally, the concentration of NSAIDs used in the present compositions ranges from about 5 percent to about 25 percent (w/w), preferably from about less than one percent (1%) to about less than twenty percent (20%).

Also included in the compositions of the present invention is at least one pharmaceutically acceptable, non-toxic dispersing agent. As used herein, the term "pharmaceutically acceptable," when referring to any or all components of the present compositions, means that such component(s) are compatible with other components therein, and not deleterious to the recipient thereof. Such dispersing agents are well known in the art and include, for example, the polymer-based dispersing agents which include, for example, polyvinylpyrrolidone (PVP; commercially known as Plasdone®), and the carbohydrate-based dispersing agents such as, for example, hydroxypropylmethylcellulose (HPMC), hydroxypropylcellulose (HPC), and the cyclodextrins. Preferred dispersing agents include PVP K29–32, dextrins, starch, derivatized starch and dextrans, while of the dextrins, derivatized cyclodextrins are especially preferred. Of such cyclodextrins, hydroxypropyl β-cyclodextrin and γ-cyclodexrin are especially preferred. The numbers relate to the molecular weight of the polymer wherein, for example, PVP K-30 has an average molecular weight of about 30,000, with attendant viscosity characteristics. Dispersing polymers generally are selected to ensure appropriate uniformity using viscosity while providing a pharmaceutically elegant appearance to the resulting solution.

The ratio of Active Ingredient or Active Ingredients to a polymer-based dispersing agent is from about 3 to about 1

(w/w) to about 1 to about 50 (w/w). A more preferred ratio is from about 2 to about 1 (w/w) to about 1 to about 20 (w/w). For compositions of the present invention containing at least one NSAID as an Active Ingredient, the preferred ratio of NSAID to polymer-based dispersing agent is from about 1 to about 1 (w/w) to about 1 to about 5 (w/w).

The ratio of Active Ingredient to a carbohydrate-based dispersing agent is from about 3 to about 1 (w/w) to about 1 to about 30 (w/w), with a generally preferred range from about 2 to about 1 (w/w) to about 1 to about 10 (w/w). For compositions of the present invention containing at least one NSAID as an Active Ingredient, the preferred ratio of NSAID to carbohydrate-based dispersing agent is from about 1 to about 1 (w/w) to about 1 to about 3 (w/w).

For the present compositions, one or more dispersing agents can be used to obtain the ratios of Active Ingredient to dispersing agent as set forth above.

Another required component of the compositions of the present invention is at least one pharmaceutically acceptable non-toxic solubilizing agent. Such readily available solubilizing agents are well known in the art and is typically represented by the family of compounds known as polyethylene glycols (PEG) having molecular weights from about 200 to about 8,000. For compositions of the present invention when a liquid is desired for the final formulation or a liquid is to be used to fill soft capsules, preferably soft gelatin capsules, preferred molecular weights range from about 200 to about 600 with PEG 400 being especially preferred. For composition of the present invention when a semi-solid is preferred, especially for filling a hard capsule, preferably a hard gelatin capsule, preferred molecular weight is about 3350 while an especially preferred molecular weight is 3350 plus sufficient 400 molecular weight PEG to improve capsule filling characteristics.

Another solubilizing agent which may be utilized in compositions of the present invention is water, especially purified, and most preferably, deioniozed. For such compositions, the concentration of water is from about zero percent to about ninety-nine percent (w/w). More particularly for compositions of the present invention to be filled into soft capsules, a maximum water concentration from about 0% to about 5% is preferred, although the concentration of total solubilizing agent may be the full concentration range taught herein.

As used in the present compositions, the concentration of the sum of solubilizing agent utilized, wherein more than one plasticizing agent can be utilized, is from about 0 percent gust greater than zero) to about 99 percent (w/w). The preferred concentration of solubilizing agent in the present compositions is from about 60 percent to about 90 percent (w/w).

One optional component of compositions of the present invention, but which should be used when such compositions are to be filled in soft gelatin capsules, is at least one pharmaceutically acceptable, non-toxic plasticizing agent. Such plasticizing agents, which are well known in the pharmaceutical formulation art, include, for example, glycerin, propylene glycol, and sorbitol. Such commercially available plasticizers can be prepared to include more than one plasticizing agent component, but the preferred plasticizing agent for the present compositions is glycerin. In addition to its use as a plasticizing agent, propylene glycol can be used as a solubilizing agent when used alone or in combination with another solubilizing agent as taught herein.

As used in the present invention, the concentration of the sum of plasticizing agent utilized, wherein more than one plasticizing agent can be utilized, is from about zero percent Oust greater than zero) to about 75 percent (w/w). The preferred of plasticizing agent is from about zero percent (0%) to about fifty percent (50%), and an especially preferred concentration in a range from about one percent (1%) to about thirty percent (30%). When the compositions of the present invention are used to fill soft gelatin capsules, the preferred concentration of such plasticizing agent is from about 5 percent to about 10 percent (w/w). Such plasticizers are especially useful with soft gelatin capsule preparations because, without which, such capsules tend to harden and lose their beneficial properties by, potentially, cracking or becoming brittle.

Another optional component of the present compositions, which is a preferred component, is at least one pharmaceutically acceptable, non-toxic, surfactant, preferably a non-ionic surfactant. Such surfactants are well known in the pharmaceutical formulation art and include readily available surfactants having a concentration from about zero percent to about 90 percent such as, for example, macro gel esters (Labrafils), Tandem 522®, Span 80®, Gelucieres® such as, for example, tocopherol polyethylene glycol 1000 succinate, polysorbate 20, and polysorbate 80. Of these, polysorbate 20 and polysorbate 80 are preferred.

As used in the present invention, the concentration of the sum of non-ionic surfactant utilized, wherein more than one such surfactant can be utilized, is from about zero percent to about 10 percent (w/w), with a range from about 1 percent to about 5 percent (w/w) being preferred. An especially preferred concentration is about 3 percent,(w/w).

Typically, the order of addition of the various components comprising the present invention will not affect the formation of a solution, when desired, of the present invention. However, when such a surfactant is used, it may be best to add the surfactant or surfactants following addition of Active Ingredient and dispensing agent as taught herein. The order of addition of such components is likely to be more critical with the preparation of NSAID formulations of the present invention, particularly with diclofenac when used as such NSAID.

It should be understood that each component comprising the compositions of the present invention must be pharmaceutically acceptable and utilized in a non-toxic concentration.

Furthermore, when a desired Active Ingredient used in the compositions of the present invention is known to degrade in an acid medium (e.g., acid labile compounds including, for example, proton pump inhibitors including, for example, those represented by the chemical class including lansoprazole and omeprazole) it is preferred to dissolve such Active Ingredient in a strongly basic solution having a pH of at least 9.0, and maintaining a pH of at least 9.0 during preparation of composition of the present invention. However, a pH of 9.0 or higher may prohibit the filling of soft gelatin capsules. Accordingly, compositions of the present invention for which a higher pH (e.g., greater than pH about 7.5 to about 9.0) is required, should best be used to fill, when desired, hard capsules as described herein.

Typically, for such an acid labile compound, at least one dispersing agent and at least one solubilizing agent and, optionally, one or more plasticizing agent and a lower ($C_1$–$C_4$) alkanol are mixed and stirred, with heat when necessary to dissolve the dispersing agent. Generally, a constant temperature of about 40° C. tu to about 50° C., with stirring for about 30 minutes is sufficient to place these excipients into solution. To this solution is added a base, preferably a strong base including, for example, sodium hydroxide, ammonium hydroxide, potassium hydroxide, magnesium hydroxide, calcium hydroxide, and the like, in sufficient quantity to raise the pH of the solution to a pH of at least 9.0. To this solution is added one or more Active Ingredient including the acid labile Active Ingredient. Such Active Ingredient should be added slowly and intermittently while the pH of the resulting solution is monitored and maintained at a pH of at least 9.0 by adding, as needed, additional base as taught above. Once the desired concentration of Active Ingredient is reached and the pH is maintained at a pH of at least 9.0, one or more optional surfactant, preferably a non-ionic surfactant, and/or one or more optional plasticizing agent may be added. Following preparation of this composition of the present invention, the solution may be converted to a semi-solid via methods well known to one of ordinary skill in the art, or may be filled into capsules, hard or soft, as appropriate. The concentration of the Active lngredient(s) and each excipient are as set forth herein. A preferred Active Ingredient for use in this process is one or more proton pump inhibitor which are known to those of ordinary skill in the art, of which omeprazole is especially preferred.

Additionally, capsules filled with pharmaceutical compositions prepared by the above-described process, or any capsule containing a pharmaceutical composition of the present invention, may be coated, where appropriate with, for example, omeprazole, with any non-toxic, pharmaceutically acceptable coating. Such coatings include, for example, enteric, taste-masking, color-coating, sustained or delayed release, non-performance flavor coatings, and the like, and are prepared and applied via techniques well known to one of ordinary skill in the art. Preferably, capsules containing pharmaceutical composition of the present invention in which the Active Ingredient is omeprazole are enterically coated.

This process provides the surprising result of maintaining said Active Ingredient in solution during the process, resulting in a stable pharmaceutical composition of the present invention with its attending benefits as set forth herein.

Accordingly, another aspect of the present invention provides a process for preparing a pharmaceutical composition of the present invention wherein said at least one acid moiety of said one or more pharmaceutically active agent is acid labile comprising:

forming a solution of at lest one dispersing agent and at least one solubilizing agent, and, optionally, one or more lower ($C_1$–$C_4$) alkanol;

adding sufficient base to establish said solution at a pH of at least 9.0; and adding said one or more pharmaceutically active agent while maintaining said solution at a pH of at least 9.0; and, optionally, one or more surfactant; and, further optionally, one or more plasticizing agent.

Another aspect of the present invention provides a pharmaceutical composition when prepared by the above-described process.

Other pharmaceutically acceptable, non-toxic pharmaceutical additives may be included in the compositions of the present invention and include, for example, sweetening agents, local anesthetics, antibacterials, a lower alkyl alcohol such as ethanol, and the like.

Commonly used pharmaceutical agents, such as, for example, about 0.1 N to 2N hydrochloric acid, are used to adjust the pH of the composition and/or, when at least one Active Ingredient is in the form of a salt, generally an alkali metal salt, to convert the Active Ingredient to the free acid. A preferred pH range of the present compositions when used for filling soft gelatin capsules is from about 4.0 to about 9.0.

Accordingly, the novel compositions of the present invention provide beneficial pharmaceutical properties while utilizing a minimum number of components.

Typically, an oral solution containing one or more Active Ingredients will mix with stomach acid, agglomerate, and form a sediment in a brief period of time, making the Active Ingredient less biologically available. The compositions of the present invention, with minimum ingredients of at least one of each of the following: Active Ingredient, dispersing agent and solubilizing agent, and, optionally, a surfactant and, further optionally, a plasticizing agent each as described above, preferably when the present compositions are used to fill non-toxic, pharmaceutically acceptable capsules of which soft gelatin capsules and hard gelatin capsules are especially preferred, provides novel liquid pharmaceutical compositions. Such compositions improve the dispersing properties of the Active Ingredient upon contact with stomach acid, which results in faster, reproducible, and a more uniform absorption rate than pharmaceutical compositions outside of the scope of the present invention. A more rapid, uniform absorption of the Active Ingredients commonly provides a more rapid onset of the therapeutic benefits respectively provided by each Active Ingredient.

NSAIDs are known to cause gastrointestinal irritation, typically in the form of peptic ulceration, bleeding, and perforation. Because of the improved dispersion and absorption properties of the compositions of the present invention, such compositions inhibit such gastroirritation induced via the chronic use of such NSAIDs. As used herein, the term "inhibit" is defined to include its generally accepted meaning and includes, without limitation, a reduction, holding in abeyance, and/or minimizing the gastroirritation in a mammal induced and/or resulting from the administration of one or more NSAID to a mammal compared to such gastroirritation induced and/or resulting from the administration of conventional pharmaceutical formulations of NSAIDs.

Surprisingly, particularly in light of the discussion found in the above-referenced U.S. Pat. No. 5,183,829, the addition of at least one surfactant, particularly a non-ionic as described above, to the compositions of the present invention, improved the dispersion properties of the Active Ingredients over compositions of the present invention not containing such non-ionic surfactant. Accordingly, compositions of the present invention which include such a surfactant, particularly those containing one or more NSAIDs as an Active Ingredient, also provide more rapid onset of the therapeutic benefits respectively provided by each Active Ingredient. Such compositions containing such a surfactant also inhibit gastroirritation in a mammal induced and/or resulting from the administration of a composition of the present invention wherein the Active Ingredient is at least one NSAID compared to such gastroirritation induced and/or resulting from the administration of conventional pharmaceutical formulations of NSAIDs.

As such, another aspect of the present invention provides a method of improving the rate of absorption of Active Ingredients in mammals, particularly humans, comprising administering to a mammal in need of the treatment with such Active Ingredient a composition of the present invention.

An additional aspect of the present invention provides a method of accelerating the onset of the therapeutic benefit in mammals, particularly humans, respectively provided by each Active Ingredient comprising administering to a mammal in need of the treatment with such Active ingredient a composition of the present invention.

The compositions of the present invention are usually formulated to deliver a typical, non-toxic daily dosage level of from about 0.25 mg to about 400 mg per day of Active Ingredient. Preferred doses for each Active Ingredient used in the compositions of the present invention will, of course, be determined by the particular circumstances surrounding the case including, for example, an attending physician considering the state of being of the patient and the severity of the pathological condition being treated. Preferred daily doses wherein the Active Ingredient is an NSAID, or a pharmaceutically acceptable salt thereof, will be from about 10 mg to about 2,000 mg per day. Typically, the oral compositions of the present invention are formulated to deliver about 10 mg to 500 mg per teaspoon of a liquid product.

The liquid or semi-solid compositions of the present invention are also used to fill capsules, particularly hard gelatin capsules and, especially, soft gelatin capsules wherein the amount of Active Ingredient in each such capsule is from about 10 mg to about 250 mg. The preparation of such capsules is well known in the pharmaceutical art [see, e.g. *Modem Pharmaceutics, Third Edition*, (G. S. Banker and C. T. Rhodes, ed.; 1996); and *The Theory and Practice of Industrial Pharmacy, Third Edition*, (L. Lachman, H. A. Liebernan, and J. L. Kanig, ed.; 1986)].

Accordingly, another aspect of the present invention provides a method of treating mammals in need of the treatment provided by one or more Active Ingredients, or a pharmaceutically acceptable salt thereof, comprising administering to said mammal, particularly a human, a composition of the present invention wherein said composition contains at least one Active Ingredient. Preferred Active Ingredients include one or more NSAID, particularly diclofenac, sulindac, or indomethacin, for the treatment of a mammal in need of anti-inflammatory and/or analgesic treatment, omeprazole for the inhibition of gastric acid secretion, and the antihistamine fexofenadine. A further aspect of the present invention provides such method of treatment as set forth in this paragraph wherein a composition of the present invention is orally administered to such mammal contained as a liquid or within a soft or hard gelatin capsule.

Because of the unique in vivo pharmacodynamics of compositions of the present invention, such compositions, particularly wherein at least one Active Ingredient is a NSAID, preferably diclofenac, indomethacin, or sulindac, demonstrate enhanced activity such that otherwise unattainable clinical results are provided. For example, NSAIDs are not commonly recognized to provide relief from severe paroxysmal headaches, particularly migraine headaches. However, compositions of the present invention in which the Active Ingredient is at least one NSAID provide more rapid relief from migraine headaches when orally administered at a single dosage of from about 10 mg to about 2,000 mg, preferably from about 50 mg to about 250 mg, repeated at intervals of from about 2 to about 4 hours, as needed, compared to existing formulations containing the same pharmaceutically active ingredient. Such relief from migraine headaches are also attainable by administration of such compositions administered in combination with, concurrent to or, preferably, subsequent to the administration of a motility agent such as, for example, metoclopromide. When administered concurrent to the administration of such a composition of the present invention, such a motility agent can be included as an optional ingredient in such composition of the present invention. Typically, metoclopromide will be effective as a motility agent when so administered at a dosage range from about 5 mg to about 15 mg for each administration of such a composition of the present invention.

Accordingly, another aspect of the present invention provides a method of treating paroxysmal headaches, particularly migraine headaches comprising administering to a mammal, typically humans, in need of such treatment, a composition of the present invention, preferably in capsule form, and especially in soft gelatin capsule form, wherein said Active Ingredient is an effective amount of at least one NSAID, or a pharmaceutically acceptable salt thereof, preferably diclofenac, sulindac, or indomethacin and, optionally an effective amount of a motility agent, preferably metoclopramide.

Furthermore, compositions of the present invention in which the Active Ingredient is at least one NSAID, preferably administered in combination with, concurrent to, or subsequent to the administration of a motility agent as taught above, provides more rapid relief from pain, as a general analgesic, and particularly from injury or from surgical procedures such a dental surgery, hysterectomy, and arthroscopy. In addition to the analgesic effect of such compositions, such compositions, wherein the Active Ingredient is at least one NSAID, also provide more rapid relief from inflammation caused by injury, stress, surgical procedures, and the like. The dosage regime and dosage strength for using such compositions of the present invention for analgesic and anti-inflammation are as set forth above for the treatment of paroxysmal headache.

Accordingly, another aspect of the present invention provides a method of treating pain and for treating inflammation in a mammal, preferably a human, comprising administering to a mammal in need of treatment a composition of the present invention, preferably in capsule form, and especially in soft gelatin capsule form, wherein said Active Ingredient is an effective amount of at least one NSAID, or a pharmaceutically acceptable salt thereof, preferably diclofenac, sulindac, or indomethacin, and, optionally, an effective amount of a motility agent, preferably metoclopramide.

As used herein, the term "treatment", or a derivative thereof, contemplates partial or complete inhibition of the stated disease state such as, for example, pain, when a composition of the present invention is administered prophylactically or following the onset of the disease state for which such composition of the present invention is administered.

Another aspect of the present invention provides a method of inhibiting gastric acid secretion comprising administering to a mammal, typically humans, in need of such treatment, a composition of the present invention, preferably in capsule form, wherein said Active Ingredient is an effective amount of a proton pump inhibitor, preferably omeprazole, or a pharmaceutically acceptable salt thereof.

An additional aspect of the present invention provides a method of providing an antihistamine effect in mammals, preferably humans, comprising administering to such mammal in need of treatment a composition of the present invention, preferably in liquid form, wherein said Active Ingredient is an effective amount of fexofenadine, or a pharmaceutically acceptable salt thereof.

Compositions of the present invention in which omeprazole, or a pharmaceutically acceptable salt thereof, is the Active Ingredient typically deliver a non-toxic daily dosage level of from about 5 mg to about 40 mg, and an especially preferred dosage of about 20 mg.

Compositions of the present invention in which fexofenadine, or a pharmaceutically acceptable salt thereof, is the Active Ingredient typically deliver a non-toxic daily dosage level of from about 30 mg to about 120 mg, and an especially preferred dosage of about 60 mg.

Also provided are compositions of the present invention comprising an effective amount of at least a first Active Ingredient which is a NSAID, or a pharmaceutically acceptable salt thereof, preferably diclofenac, sulindac, or indomethacin, and an effect amount of at least a second ingredient which is a motility agent, or a pharmaceutically acceptable salt thereof, particularly metoclopramide.

The following analytical procedures were used to examine the behavior of Active Ingredients upon contact with acid media which is recognized in the art as simulated gastric fluid (SGF), without enzymes:

A. Visual Dispersion

To a clear, 400 mL glass beaker was added 100 mL or 150 mL of 0.1N hydrochloric acid. To the acid was added 1 mL of a composition of the present invention, as the mixture was vigorously stirred, and the dispersion behavior was observed. Visual observations included uniformity, agglomeration, relative time to agglomeration, and the like. Visual observations confirmed that compositions of the present invention had improved dispersion properties and tended to have less agglomeration.

B. Light Transmittance

To a clear, 400 mL glass beaker was added 150 mL of 0.1N hydrochloric acid. To the acid was added about 1 mL of a composition of the present invention, and the mixture was stirred at a constant speed. During mixing, the resultant solution was pumped through a Hewlett-Packard (Roseville, Calif.) spectrophotometer equipped with a 1 cm cell set on percent transmittance at a wave length of 530 nm. Results demonstrated that percent light transmittance with compositions of the present invention, particularly those compositions including at least one non-ionic surfactant, was less than compositions outside the scope of the present invention. These data confirm that compositions of the present invention provide greater dispersion of Active Ingredients than the reference formulations.

C. Turbidity

To a glass vial sampler provided with the Turbidimeter model 2100AN marketed by Hach (Loveland, Colo.) was added 30 mL of 0.1N hydrochloric acid. To the acid was added 0.1 g of a composition of the present invention. The mixture was vigorously shaken and turbidity of the mixture was measured in Nephelometric Turbidity Units (NTU). Turbidity was measured at various time intervals using, for example, one of the following regimens: (i) 30, 45, 60, 75, 90 and 120 minutes; (ii) 10, 20, 30, and 45 seconds and once each minute from 1 minute to 15 minutes; and (iii) 10 and 30 seconds, and 3, 5, 10, 15, 20, 30, and 60 minutes.

Results substantiated that the compositions of the present invention provided for greater dispersion and less agglomeration in simulated gastric fluid than compositions outside of the scope of the present invention.

The following embodiments of the invention are designed to illustrate and teach the specific use of the invention, but are not intended to be limiting to the scope of the invention in any respect, and should not be so construed.

EXAMPLE 1

Preparation of Liquid Diclofenac Sodium Composition

To a 100 mL glass beaker was added 35.95 g of polyethylene glycol 400 (PEG 400) and the PEG 400 was stirred using a stirbar on a stirplate, with heat maintained between about 45–55° C. To the beaker was slowly added 3.15 g of PVP K29–32. Upon complete dissolution (visual observation) of the PVP K29–32, 3.15 g of diclofenac sodium was added, and the mixture was allowed to cool to ambient temperature, then 1.5 g of polysorbate 80 was added. This mixture was stirred for about two minutes, 5.0 g of glycerin was added while the mixture was stirred for about two additional minutes, then 1.25 g of hydrochloric acid was added resulting in a slightly hazy solution. This mixture was stirred for about an additional 10–15 minutes. This composition is administered as an oral solution or is used to fill soft gelatin capsules using standard procedures.

EXAMPLE 2

Using the preparation from Example 1, the following composition was prepared:

|  | % w/w |
|---|---|
| Diclofenac Sodium | 6.3 |
| Polyethylene Glycol 400 | 71.9 |
| 2NHydrochloric Acid | 2.5 |
| Glycerin | 10.0 |
| Polysorbate 80 | 3.0 |
| PVP K29-32 | 6.3 |
|  | 100.0% |

EXAMPLE 3

Preparation of Liquid Cromolyn Sodium Composition

To a 100 mL glass beaker was added 37.0 g of polyethylene glycol 400 (PEG 400), and the PEG 400 was stirred using a stirbar on a stirplate, with heat maintained between about 45–55° C. To the beaker was added 5.0 g of glycerin, while stirring continued for about 2 minutes, then 2.5 g of purified water was added and the mixture was stirred for about an additional 2–3 minutes. To the mixture was then added 2.0 g of PVP K29–32 with stirring until the PVP K29–32 was completely dissolved (visual observation). Then, 2.0 g of cromolyn sodium was added and the mixture was stirred until the cromolyn sodium was completely dissolved (visual observation). The mixture was allowed to cool to ambient temperature before adding 1.5 g of polysorbate 80. This mixture was stirred for about 10–15 minutes, resulting in a slightly hazy solution. This composition is administered as an oral solution or is used to fill soft gelatin capsules using standard procedures.

EXAMPLE 4

Using the preparation from Example 3, the following composition was prepared:

|  | % w/w |
|---|---|
| Cromolyn Sodium | 4.0 |
| Polyethylene Glycol 400 | 74.0 |
| Purified Water | 5.0 |
| Glycerin | 10.0 |
| Polysorbate 80 | 3.0 |
| PVP K29-32 | 4.0 |
|  | 100.0% |

EXAMPLE 5

Preparation of Liquid Sulindac Composition

To a 100 mL glass beaker was added 31.09 of polyethylene glycol 400 (PEG 400), and the PEG 400 was stirred using a stirbar on a stirplate, with heat maintained between about 55–65° C. To the beaker was added 5.0 g of glycerin, while stirring continued for about 2 minutes, then 2.5 g of purified water was added and the mixture was stirred for about an additional 2–3 minutes. To the mixture was then slowly added 5.0 g of PVP K29–32 with stirring continued until the PVP K29–32 was completely dissolved (visual observation). Then, 5.0 g of sulindac was added and the mixture was stirred until the sulindac was completely dissolved (visual observation). The mixture was allowed to cool to ambient temperature before adding 1.5 g of polysorbate 80. The mixture was stirred for about 10–15 minutes, resulting in a slightly hazy solution. This composition is administered as an oral solution or is used to fill soft gelatin capsules using standard procedures.

EXAMPLE 6

Using the preparation from Example 5, the following composition was prepared:

|  | % w/w |
|---|---|
| Sulindac | 10.0 |
| Polyethylene Glycol 400 | 62.0 |
| Purified Water | 5.0 |
| Glycerin | 10.0 |
| Polysorbate 80 | 3.0 |
| PVP K29-32 | 10.0 |
|  | 100.0% |

EXAMPLE 7

Preparation of Liquid Gemfibrozil Composition

To a 100 mL glass beaker was added 27.25 g of polyethylene glycol 400 (PEG 400) and the PEG 400 was stirred using a stirbar on a heated stirplate, with heat maintained between about 45–55° C. To the beaker was slowly added 7.5 g of PVP K29–32. Upon complete dissolution (visual observation) of the PVP K29–32, 7.5 g of gemfibrozil was slowly added with stirring until the gemfibrozil was completely dissolved (visual observation). The mixture was allowed to cool to ambient temperature, then 1.5 g of polysorbate 80 was added. This mixture was stirred for about two minutes, resulting in a slightly hazy solution. To this mixture was then added 5.0 g of glycerin while stirring continued for about two minutes, and then 1.25 g of purified water was added and the solution was stirred for an additional 10–15 minutes. This composition is administered as an oral solution or is used to fill soft gelatin capsules using standard procedures.

EXAMPLE 8

Using the preparation from Example 7, the following composition was prepared:

|  | % w/w |
|---|---|
| Gemfibrozil | 15.0 |
| Polyethylene Glycol 400 | 54.5 |
| Purified Water | 2.5 |
| Glycerin | 10.0 |
| Polysorbate 80 | 3.0 |

-continued

|  | % w/w |
|---|---|
| PVP K29-32 | 15.0 |
|  | 100.0% |

EXAMPLE 9

Preparation of Diclofenac Sodium Composition

To a 100 mL glass beaker was added 37.45 g of polyethylene glycol 400 (PEG 400) and the PEG 400 was stirred using a stirbar on a stirplate, with heat maintained between about 45–55° C. To the beaker was slowly added 3.15 g of PVP K29–32. Upon complete dissolution (visual observation) of the PVP K29–32, 3.15 g of diclofenac sodium was slowly added with stirring until the diclofenac sodium was completely dissolved (visual observation). The mixture was allowed to cool to ambient temperature. This mixture was stirred for about two minutes, resulting in a slightly hazy solution. To this mixture was then added 5.0 g of glycerin while the mixture was stirred for about two minutes, then 1.25 g of hydrochloric acid 2.0N was added and the solution was stirred for an additional 10–15 minutes. This composition is administered as an oral solution or is used to fill soft gelatin capsules using standard procedures.

EXAMPLE 10

Using the preparation from Example 9, the following composition was prepared:

|  | % w/w |
|---|---|
| Diclofenac Sodium | 6.3 |
| Polyethylene Glycol 400 | 74.9 |
| 2N Hydrochloric Acid | 2.5 |
| Glycerin | 10.0 |
| PVP K29-32 | 6.3 |
|  | 100.0% |

EXAMPLE 11

Preparation of Liquid Gemfibrozil Composition

To a 100 mL glass beaker was added 28.75 g of polyethylene glycol 400 (PEG 400), and the PEG 400 was stirred using a stirbar on a stirplate, with heat maintained between about 45–55° C. To the mixture was slowly added 7.5 g of PVP K29–32 with stirring continued until the PVP K29–32 was completely dissolved (visual observation). To the mixture was then slowly added 7.5 g of gemfibrozil and the mixture was stirred until the gemfibrozil was completely dissolved (visual observation). The mixture was allowed to cool to ambient temperature before adding 5.0 g of glycerin. The mixture was stirred for about 2 minutes and then 1.25 g of purified water was added, while stirring continued for about 10–15 minutes. This composition is administered as an oral solution or is used to fill soft gelatin capsules using standard procedures.

EXAMPLE 12

Using the preparation from Example 11, the following composition was prepared:

|  | % w/w |
|---|---|
| Gemfibrozil | 15.0 |
| Polyethylene Glycol 400 | 57.5 |
| Purified Water | 2.5 |
| Glycerin | 10.0 |
| PVP K29-32 | 15.0 |
|  | 100.0% |

EXAMPLE 13

Preparation of Liquid Gemfibrozil Composition

To a 100 mL glass beaker was added 35 mg of polyethylene glycol 400 (PEG 400), and the PEG 400 was stirred using a stirbar on a stirplate, with heat maintained between about 45–55° C. To the mixture was slowly added 7.5 g of PVP K29–32 with stirring continued until the PVP K29–32 was completely dissolved (visual observation). To the mixture was then slowly added 7.5 g of gemfibrozil and the mixture was stirred until the gemfibrozil was completely dissolved (visual observation). The mixture was allowed to cool to ambient temperature. This composition is administered as an oral solution or is used to fill soft gelatin capsules using standard procedures.

EXAMPLE 14

Using the preparation from Example 13, the following composition was prepared:

|  | % w/w |
|---|---|
| Gemfibrozil | 15.0 |
| Polyethylene Glycol 400 | 70.0 |
| PVP K29-32 | 15.0 |
|  | 100.0% |

EXAMPLE 15

Preparation of Liquid Diclofenac Composition

To a 100 mL glass beaker was added 43.7 mg of polyethylene glycol 400 (PEG 400), and the PEG 400 was stirred using a stirbar on a stirplate, with heat maintained between about 45–55° C. To the mixture was slowly added 3.15 g of PVP K29–32 with stirring continued until the PVP K29–32 was completely dissolved (visual observation). To the mixture was then slowly added 3.15 g of diclofenac and the mixture was stirred until the diclofenac was completely dissolved (visual observation). The mixture was allowed to cool to ambient temperature. This composition is administered as an oral solution or is used to fill soft gelatin capsules using standard procedures.

EXAMPLE 16

Using the preparation from Example 15, the following composition was prepared:

|  | % w/w |
|---|---|
| Diclofenac | 6.3 |
| Polyethylene Glycol 400 | 87.4 |
| PVP K29-32 | 6.3 |
|  | 100.0% |

EXAMPLE 17

Preparation of Liquid Cromolyn Sodium Composition

To a 100 mL glass beaker was added 46 mg of polyethylene glycol 400 (PEG 400), and the PEG 400 was stirred using a stirbar on a stirplate, with heat maintained between about 45–55° C. To the mixture was slowly added 2.0 g of PVP K29–32 with stirring continued until the PVP K29–32 was completely dissolved (visual observation). To the mixture was then slowly added 2.0 g of cromolyn sodium and the mixture was stirred until the cromolyn sodium was completely dissolved (visual observation). The mixture was allowed to cool to ambient temperature. This composition is administered as an oral solution or is used to fill soft gelatin capsules using standard procedures.

EXAMPLE 18

Using the preparation from Example 17, the following composition was prepared:

|  | % w/w |
|---|---|
| Cromolyn Sodium | 4.0 |
| Polyethylene Glycol 400 | 92.0 |
| PVP K29-32 | 4.0 |
|  | 100.0% |

EXAMPLE 19

Preparation of Liquid Sulindac Composition

To a 100 mL glass beaker was added 40 mg of polyethylene glycol 400 (PEG 400), and the PEG 400 was stirred using a stirbar on a stirplate, with heat maintained between about 45–55° C. To the mixture was slowly added 5.0 g of PVP K29–32 with stirring continued until the PVP K29–32 was completely dissolved (visual observation). To the mixture was then slowly added 5.0 g of sulindac and the mixture was stirred until the sulindac was completely dissolved (visual observation). The mixture was allowed to cool to ambient temperature. This composition is administered as an oral solution or is used to fill soft gelatin capsules using standard procedures.

EXAMPLE 20

Using the preparation from Example 19, the following composition was prepared:

|  | % w/w |
|---|---|
| Sulindac | 10.0 |
| Polyethylene Glycol 400 | 80.0 |
| PVP K29-32 | 10.0 |
|  | 100.0% |

EXAMPLES 21–37

The Following Process was Used to Prepare Examples 21–37:

To a suitable stainless steel container was added polyethylene glycol (PEG) and, where appropriate, ethanol. The mixture was stirred with a Lightnin' mixer at low speed for 3 minutes. To this mixture, held at a constant temperature (40° C. to 50° C.) using a heat plate, was added polyvinylpyrrolidone and stirred with a Lightnin' mixer for at least 30 minutes or until the polyvinylpyrrolidone was completely dissolved. To this solution was added the selected Active Ingredient and the mixture was stirred for at least 20 minutes, using a Lightnin' mixer, while held at a constant temperature, not more than 50° C., until such Active Ingredient was completely dissolved. To this solution was added a non-ionic surfactant, where appropriate, and the solution was mixed with a Lightnin' mixer for about 10 minutes. The resulting liquid compositions of the present invention are administered according to the teaching provided herein, or are further prepared for filling into non-toxic, pharmaceutically acceptable capsules.

To a second suitable stainless steel container was added an excess of PEG 4600 which was heated to about 55° C. to about 60° C. Once melted, the PEG 4600 was kept stirred with a Lightnin' mixer. To the first stainless steel container was added an appropriate amount of PEG 4600 from the second stainless steel container. The solution from the first stainless steel container was maintained at a temperature from about 45° C. to about 50° C. prior to and during the addition of PEG 4600. The resulting mixture was stirred for at least 30 minutes.

Indomethacin Compositions: Ingredients are a percent of the total composition (w/w).

|  | Example Number | | | |
|---|---|---|---|---|
|  | 21 | 22 | 23 | 24 |
| Indomethacin | 8.9 | 5.0 | 8.7 | 8.3 |
| PEG 400 | 25.0 | 24.0 | 24.3 | 23.3 |
| PEG 4600 | 50.0 | 56.0 | 48.7 | 46.8 |
| PVP K29-32 | 1.8 | 1.7 | 4.3 | 8.3 |
| Tween 80 | 10.7 | 10.0 | 10.4 | 10.0 |
| Ethanol 190pf | 3.6 | 3.3 | 3.6 | 3.3 |
|  | 100.0 | 100.0 | 100.0 | 100.0 |

|  | Example Number | | |
|---|---|---|---|
|  | 25 | 26 | 27 |
| Indomethacin | 9.0 | 8.9 | 8.9 |
| PEG 400 | 25.2 | 41.1 | 82.2 |
| PEG 4600 | 50.5 | 41.1* | 0.0 |
| PVP K29-32 | 10.8 | 8.9 | 8.9 |
| Tween 80 | 0.9 | 0.0 | 0.0 |
| Ethanol 190pf | 3.6 | 0.0 | 0.0 |
|  | 100.0 | 100.0 | 100.0 |

*PEG 4600 was replaced with PEG 3350

Valproic Acid Compositions: Ingredients are a percent of the total composition (w/w).

|  | Example Number | | | |
|---|---|---|---|---|
|  | 28 | 29 | 30 | 31 |
| Valproic Acid | 40.3 | 25.3 | 25.8 | 23.2 |
| PEG 400 | 0.0 | 0.0 | 0.0 | 0.0 |
| PEG 4600 | 45.2 | 56.6 | 57.7 | 51.9 |
| PVPK 29-32 | 1.6 | 2.0 | 0.0 | 0.0 |
| Tween 80 | 9.7 | 12.1 | 12.4 | 11.1 |
| Ethanol 190pf | 3.2 | 4.0 | 4.1 | 3.8 |
|  | 100.0 | 100.0 | 100.0 | 100.0 |

|  | Example Number | | |
|---|---|---|---|
|  | 32 | 33 | 34 |
| Valproic Acid | 20.6 | 12.5 | 12.5 |
| PEG 400 | 0.0 | 37.5 | 75.0 |
| PEG 4600 | 46.2 | 37.5* | 0.0 |
| PVP K29-32 | 20.0 | 12.5 | 12.5 |
| Tween 80 | 9.9 | 0.0 | 0.0 |
| Ethanol 190pt | 3.3 | 0.0 | 0.0 |
|  | 100.0 | 100.0 | 100.0 |

*PEG 4600 was replaced with PEG 3350

Diclofenac Sodium Compositions: Ingredients are a percent of the total composition (w/w).

|  | Example Number | | |
|---|---|---|---|
|  | 35 | 36 | 37 |
| Diclofenac Sodium | 5.1 | 5.1 | 5.1 |
| PEG 400 | 24.4 | 44.9 | 89.8 |
| PEG 4600 | 57.0 | 49.9* | 0.0 |
| PVP K29-32 | 0.0 | 5.1 | 5.1 |
| Tween 80 | 10.2 | 0.0 | 0.0 |
| Ethanol 190pf | 3.3 | 0.0 | 0.0 |
|  | 100.0 | 100.0 | 100.0 |

*PEG 4600 was replaced with PEG 3350

EXAMPLE 38

For the compositions set forth above, replace the stated Active Ingredient with fexofenadine.

EXAMPLE 39

Process for Preparing a Composition in which Omeprazole is the Active Ingredient

Solution Preparation

To a suitable first vessel was added 264.0 g of polyethylene glycol (PEG) 400, NF and 38.0 g of ethanol, 190 proof, USP. To this solution, which was continuously stirred with a Lightnin' mixer was added 19.0 g of PVP K29–32. The excipients were mixed for at least 30 minutes and a water bath was used to maintain a constant temperature between 40° C. and 50° C. The pH of the resulting solution was adjusted to pH 13.5 using 8M sodium hydroxide. To this buffered solution was slowly and intermittently added 38.0 g of omeprazole, while the pH was continuously monitored and adjusted to maintain a pH of at least 9.0 via the dropwise addition of 8M sodium hydroxide. To this solution was added 113.0 g of polysorbate 80,NF, and the resulting solution was moderately stirred for 10 minutes using a Lightnin' mixer.

Capsule Preparation

To a suitable second vessel was added an excess (600 g) of the required amount of PEG 3350. The PEG 3350 was heated in a water bath to maintain a temperature of about 55° C. to about 60° C., and stirred with a Lightnin' mixer, until the PEG 3350 was melted. To the first vessel was added 528.0 g of PEG 3350 from the second vessel, and the temperature of the mixture in the first vessel was maintained at a temperature of 40° C. to 50° C. while the mixture was stirred for at least 30 minutes. The pH of the resulting solution was maintained at a pH of about 10.0 (pH 9.8–10.2) via the addition of 8M sodium hydroxide solution. Number one capsule bodies were filled while the solution was continuously stirred and maintained at a temperature of 45° C. to 55° C. during filling. After capping, the resulting capsules weighed from 575 g to 635 g (gross weight). Each size one capsule was then placed in a size zero capsule for coating.

In addition, these preparations were made using 1.9 g of omeprazole, 15.4 g of PEG 400, 30.8 of PEG 3350, and 1.9 g of PVP K29–32 in lieu of measurements described for the Active Ingredient and excipients as set forth in this example 39.

Capsule Coating

To a first glass vessel was added 440.0 g of acetone,NF, which was stirred to maintain a moderate vortex with a Lightnin' mixer. To the acetone was added 10.0 g of triethyl citrate,NF, and mixed for 2 minutes, followed by the slow addition of 50.0 g Eudragit® L100 with continued mixing for 10 minutes or until a uniform dispersion was achieved. To a second glass vessel was added an aliquot of the mixture from the first glass vessel. With moderate stirring, using a stir bar, the zero size capsules were partially hand dipped, allowed to dry, and the uncoated part of such capsule was then hand dipped and allowed to dry. Each capsule was given 3 complete coats using the procedure taught above. Alternatively, other coatings known to one of ordinary skill in the art including, for example, pan coating, spray coating, and the like, are used.

We claim:

1. A pharmaceutical composition comprising:
   one or more pharmaceutically active agent wherein said pharmaceutically a active agent is selected from the group consisting of said agents wherein at least one of said agents having at least one acid moiety, and at least one of said agents having at least one ester group or other chemically active moiety in which the terminal moiety to said ester group or other chemically active moiety is hydrolyzed or otherwise removed in situ or in vivo forming at least one acid moiety; and wherein said pharmaceutically active agent is soluble in acid at a ratio of about 3:1 (acid to solute) to about 10,000:1 (acid to solute) or a pharmaceutically acceptable salt thereof;
   at least one dispersing agent selected from the group consisting of polymer-based dispersing agents and carbohydratebased dispersing agents, wherein the ratio of said one or more pharmaceutically active agent to said at least one polymer-based dispersing agent is from about 3:1 (w/w) to about 1:50 (w/w) and wherein the ratio of said one or more pharmaceutically active agent to said at least one carbohydrate-based dispersing agent is from about 3:1 (w/w) to about 1:20 (w/w); and
   at least one solubilizing agent; and, optionally,
   at least one surfactant; and further optionally,
   at least one plasticizing agent.

2. A pharmaceutical composition according to claim 1 wherein said one or more polymer-based dispersing agent is polyvinylpyrrolidone.

3. A pharmaceutical composition according to claim 2 wherein said polyvinylpyrrolidone is polyvinylpyrrolidone K29–32.

4. A pharmaceutical composition according to claim 1 wherein said one or more carbohydrate-based dispersing agent is selected from the group consisting of hydroxypropylcellulose, hydroxypropylmethylcellulose, and cyclodextrin.

5. A pharmaceutical composition according to claim 1 wherein the concentration of said one or more solubilizing agent is from about zero percent to about 99 percent (w/w) of the total composition.

6. A pharmaceutical composition according to claim 5 wherein said one or more solubilizing agent is selected from the group consisting of water and polyethylene glycol.

7. A pharmaceutical composition according to claim 6 wherein the molecular weight of said polyethylene glycol is from about 200 to about 8,000.

8. A pharmaceutical composition according to claim 6 wherein the concentration of said polyethylene glycol is from about 20 percent to about 99 percent (w/w) of the total composition.

9. A pharmaceutical composition according to claim 5 wherein the concentration of said water is from about zero percent to about 99 percent (w/w) of the total composition.

10. A pharmaceutical composition according to claim 1 wherein said one or more pharmaceutically active agent is selected from the group consisting of non-steroidal anti-inflammatory drugs, quinapril, fluvastatin, lovastatin, pravastatin, cervistatin, atorvastin, simvastatin, fexofenadine, cromolyn, omeprazole, gemfibrozil, ciprofibrate, ciprofloxacin, lomeflloxacin, ofloxacin, carbidopa, levodopa, retinoic acid, carboprost, penicillins, beta lactams, cephalosporins, liothryonine and probenecid.

11. A pharmaceutical composition according to claim 10 wherein said non-steroidal anti-inflammatory drugs are selected from the group consisting of aralkylcarboxylic acids and arylcarboxylic acids.

12. A pharmaceutical composition according to claim 11 wherein said aralkylcarboxylic acids are selected from the group consisting of diclofenac, fenoprofen, flurbiprofen, ibuprofen, indomethacin, ketoprofen, ketorolac, naproxen, sulindac, etodolac, and tometin.

13. A pharmaceutical composition according to claim 11 wherein said arylcarboxylic acids are selected from the group consisting of diflunisal, mefenamic acid, meclofenamic acid, and flufenamic acid.

14. A pharmaceutical composition according to claim 10 wherein said penicillins are selected from the group consisting of amoxicillins and ampicillins.

15. A pharmaceutical composition according to claim 1 wherein the concentration of said optional at least one plasticizing agent is from about zero percent to about 75 percent (w/w) of the total composition.

16. A pharmaceutical composition according to claim 15 wherein said plasticizing agent is selected from the group consisting of glycerin, propylene, glycol, and sorbitol.

17. A pharmaceutical composition according to claim 5 wherein the concentration of said optional at least one plasticizing agent is from about zero percent to about 75 percent (w/w) of the total composition.

18. A pharmaceutical composition according to Claim 17 wherein said plasticizing agent is selected from the group consisting of glycerin, propylene, glycol, and sorbitol.

19. A pharmaceutical composition according to claim 15 wherein the concentration of said optional at least one surfactant is from about zero percent to about 10 percent (w/w) of the total composition.

20. A pharmaceutical composition according to claim 17 wherein the concentration of said optional at least one surfactant is from about zero percent to about 10 percent (w/w) of the total composition.

21. A method of improving the rate of absorption of one or more pharmaceutically active agent in mammals, wherein said pharmaceutically active agent is selected from the group consisting of said agent wherein:
   at least one of said agents having at least one acid moiety, and
   at least one of said agents having at least one ester or other chemically active moiety in which the terminal moiety to said ester group or other chemically active moiety is hydrolyzed or otherwise removed in situ or in vivo forming at least one add moiety; and
   wherein said pharmaceutically active agent is soluble in acid at a ratio of about 3:1 (acid to solute) to about 10,000:1 (acid to solute), or a pharmaceutically acceptable salt thereof, comprising administering to a mammal in need of treatment of said pharmaceutically active agent an effective amount of a composition according to claim 1 providing said composition comprises said optional surfactant.

22. A method of improving the onset of the therapeutic benefit of one or more pharmaceutically active agent in mammals, wherein said pharmaceutically active agent is selected from the group consisting of said agent wherein:
   at least one of said agents having at least one acid moiety, and
   at least one of said agents having at least one ester or other chemically active moiety in which the terminal moiety to said ester group or other chemically active moiety is hydrolyzed or otherwise removed in situ or in vivo forming at least one acid moiety; and
   wherein said pharmaceutically active agent is soluble in add at a ratio of about 3:1 (acid to solute) to about 10,000:1 (acid to solute), or a pharmaceutically acceptable salt thereof, comprising administering to a mammal in need of treatment of said pharmaceutically active agent an effective amount of a composition according to claim 1 providing said composition comprises said optional surfactant.

23. A method of inhibiting gastroirritation in a mammal caused by the ingestion of one or more non-steroidal anti-inflammatory drugs comprising administering a composition according to claim 1 wherein at least one of said pharmaceutically active agents is an effective amount of a non-steroidal anti-inflammatory drug.

24. A method of treating mammals in need of the treatment provided by one or more pharmaceutically active agent, wherein said pharmaceutically active agent is selected from the group consisting of said agents wherein:
   at least one of said agents having at least one acid moiety, and
   at least one of said agents having at least one ester or other chemically active moiety in which the terminal moiety to said ester or other chemically active moiety is hydrolyzed or otherwise removed in situ or in vivo forming at least on acid moiety; and
   wherein said pharmaceutically active agent is soluble in acid at a ratio of about 3:1 (acid to solute) to about 10,000:1 (acid to solute), or a pharmaceutically acceptable salt thereof, comprising administering to a mammal in need of treatment of said pharmaceutically active agent an effective amount of a pharmaceutical composition according to claim 1.

25. A method according to claim 24 wherein said pharmaceutical composition is used to fill one or more capsule, which are optionally coated, for said administration to said mammal.

26. A method according to claim 25 wherein said capsule is selected from the group consisting of soft gelatin capsules and hard gelatin capsules.

27. A method according to claim 24 wherein said one or more pharmaceutically active agent is one or more non-steroidal anti-inflammatory drugs and, optionally, a motility agent, and said mammal is in need of analgesic treatment.

28. A method according to claim 27 wherein said one or more non-steroidal anti-inflammatory drugs is selected from the group consisting of diclofenac, indomethacin, and sulindac.

29. A method according to claim 28 wherein said mammal is also in need of anti-inflammatory treatment.

30. A method according to claim 28 wherein said composition is based to fill one or more capsules, which are optionally coated, for said administration to said mammal.

31. A method according to claim 24 wherein said one or more pharmaceutically active agent is fexofenadine and said mammal is in need of antihistamine treatment.

32. A method according to claim 24 wherein said one or more pharmaceutically active agent is omeprazole and said mammal is in need of inhibition of gastric acid secretion.

33. A method according to claim 32 wherein said proton pump inhibitor is omeprazole.

34. A method according to claim 33 wherein said composition is used to fill one or more capsules, which are optionally coated, for administration to said mammal.

35. A process for preparing a pharmaceutical composition according to claim 1 wherein said at least one acid moiety of said one or more pharmaceutically active agent is acid labile comprising:

forming a solution of at least one dispersing agent and at least one solubilizing agent and, optionally, one or more lower ($C_1$–$C_4$) alkanol;

adding sufficient base to establish said solution at a pH of at least 9.0; and adding said one or more pharmaceutically active agent while maintaining said solution at a pH of at least 9.0; and optionally, one or more surfactant; and further optionally, one or more plasticizing agent.

36. A process according to claim 35 wherein the concentration of said one or more solubilizing agent is from about 0 percent to about 99 percent (w/w) of the total composition.

37. A process according to claim 35 wherein said at least one polymer-based dispersing agent is polyvinylpyrrolidone, said at least one carbohydrate-based dispersing agent is selected from the group consisting of hydroxypropylcellulose, hydroxypropylmethylcellulose, and cyclodextrin, and said at east one or more solubilizing agent is selected from the group consisting of polyethylene glycol and water.

38. A process according to claim 37 comprising the additional step of filling a capsule with pharmaceutical composition.

39. A process according to claim 38 wherein said capsule is selected from the group consisting of soft gelatin capsules and hard gelatin capsules.

40. A process according to claim 35 comprising the additional step of filling a capsule with said pharmaceutical composition.

41. A process according to claim 40 wherein said capsule is selected from the group consisting of soft gelatin capsules and hard gelatin capsules.

42. A process according to claim 35 wherein said one or more pharmaceutically active agent is a proton pump inhibitor.

43. A process according to claim 42 wherein said proton pump inhibitor is omeprazole.

44. A process according to claim 39 wherein said one or more pharmaceutically active agent is a proton pump inhibitor.

45. A process according to claim 44 wherein said proton pump inhibitor is omeprazole.

46. A pharmaceutical composition when prepared by a process according to claim 35.

47. A pharmaceutical composition according to claim 46 wherein said one or more pharmaceutically active agent is omeprazole.

48. A process according to claim 40 comprising the additional step of coating said capsule with a non-toxic, pharmaceutically acceptable coating.

49. A process according to claim 48 wherein said coating is an enteric coating.

50. A process according to claim 44 comprising the additional step of coating said capsule with a non-toxic, pharmaceutically acceptable coating.

51. A process according to claim 50 wherein said coating is an enteric coating.

52. A method according to claim 34 wherein said optional coating is an enteric coating.

53. A method according to claim 28 wherein said optional motility agent is metoclopromide.

* * * * *

UNITED STATES PATENT AND TRADEMARK OFFICE
CERTIFICATE OF CORRECTION

PATENT NO.    : 6,365,180 B1
DATED         : April 2, 2002
INVENTOR(S)   : Meyer et al.

It is certified that error appears in the above-identified patent and that said Letters Patent is hereby corrected as shown below:

Column 20,
Line 4, should read as follows:  -- pharmaceutically active agent is selected from the --

Column 21,
Line 47, should read as follows:  -- forming at least one acid moiety; and --

Column 22,
Line 2, should read as follows:  -- acid at a ratio of about 3:1 (acid to solute) to about --
Line 51, should read as follows:  -- position is used to fill one or more capsules, which are --

Column 23,
Line 19, should read as follows:  -- and cyclodextrin, and said at least one or more solubilizing --

Signed and Sealed this

Seventeenth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,365,180 B1
DATED : April 2, 2002
INVENTOR(S) : Meyer et al.

It is certified that error appears in the above-identified patent and that said Letters Patent is hereby corrected as shown below:

Column 20,
Lines 17-18, insert a -- - -- between "carbohydrate" and "based"
Line 63, delete "Iomeflloxacin" and insert -- Iomefloxacin --

Column 21,
Lines 21 and 28, delete the "," between "propylene" and -- glycol --

Column 22,
Line 25, delete "on" and insert -- one --

Signed and Sealed this

Eighth Day of June, 2004

JON W. DUDAS
*Acting Director of the United States Patent and Trademark Office*